(12) United States Patent
Lee et al.

(10) Patent No.: US 8,715,965 B2
(45) Date of Patent: May 6, 2014

(54) METHOD OF AMPLIFYING NUCLEIC ACID FROM BLOOD

(75) Inventors: Hun-joo Lee, Yongin-si (KR);
Sung-young Jeong, Yongin-si (KR);
Joon-ho Kim, Yongin-si (KR);
Kyu-youn Hwang, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 441 days.

(21) Appl. No.: 11/746,722

(22) Filed: May 10, 2007

(65) Prior Publication Data

US 2007/0281307 A1   Dec. 6, 2007

(30) Foreign Application Priority Data

Jun. 5, 2006   (KR) .................. 10-2006-0050478

(51) Int. Cl.
*C12Q 1/68* (2006.01)
*C12P 19/34* (2006.01)
*G01N 27/44* (2006.01)

(52) U.S. Cl.
USPC .......................................... 435/91.2; 435/6.1

(58) Field of Classification Search
None
See application file for complete search history.

(56) References Cited

U.S. PATENT DOCUMENTS

| | | | |
|---|---|---|---|
| 4,306,556 A | 12/1981 | Zelman | |
| 4,407,942 A | 10/1983 | Birnboim | |
| 5,437,774 A | 8/1995 | Laustsen | |
| 5,704,884 A | 1/1998 | Uemura et al. | |
| 5,935,825 A | 8/1999 | Nishimura et al. | |
| 6,284,117 B1 * | 9/2001 | Smolko et al. | ................. 204/543 |
| 6,511,831 B1 * | 1/2003 | Bernhagen et al. | .......... 435/91.1 |

FOREIGN PATENT DOCUMENTS

| | | | | |
|---|---|---|---|---|
| EP | 0752391 | * | 8/1997 | ............... C02F 1/46 |
| EP | 1672059 A1 | | 12/2005 | |
| WO | 2005083078 A1 | | 9/2005 | |
| WO | WO2005083078 | * | 9/2005 | ............. C12N 15/10 |

OTHER PUBLICATIONS (Hodgson et al., 2002, J. Mat Sci, 37, 4019-4028).*
Lyttle, D (Ulster Med J, 1962, 31(1):79-81).*
European Office Action for Application No. 07 109 428.8-2402 dated Mar. 7, 2011 (5 pages).
European Office Action for Application No. 07 109 428.8-2402 dated Nov. 22, 2011 (6 pages).
Sato, et al., "Bactericidal effect of an electrodialysis system on *E. coli* cells," Bioelectrochemistry and Bioenergetics, 21: 47-54 (1989).
European Search Report; EP07109428; Aug. 22, 2007. All the references cited in the Search Report and not previously submitted are listed above.
Disposable DNA Sample Preparation icrofluidic Chip for Nucleic Acid Probe Assay; Joon-Ho Kim, Byoung-Gyun Kim, Hyukjun Nam, Dae-Eun Park, Kwang-Seok Yun, Jun-Bo Yoon, Jichang You, Euisik Yoon; BNSDOCID: < XP.1057613A_1_>; pp. 133-136, 2002.

* cited by examiner

*Primary Examiner* — Stephanie K Mummert
(74) *Attorney, Agent, or Firm* — Cantor Colburn LLP

(57) ABSTRACT

A method of amplifying nucleic acid from blood, the method including performing an electrodialysis on a blood sample to reduce the ionic strength of the sample, and performing a Polymerase Chain Reaction ("PCR") using the blood sample on which the electrodialysis is performed as a template.

11 Claims, 4 Drawing Sheets

10  30  20  40  10

ELECTRO-DIALYSIS BEFORE            ELECTRO-DIALYSIS AFTER

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
agtgtggatt cggcactcct                                                  20

<210> SEQ ID NO 2
<211> LENGTH: 23
<212> TYPE: DNA
<213> ORGANISM: Artificial Sequence
<220> FEATURE:
<223> OTHER INFORMATION: reverse primer

<400> SEQUENCE: 2
gagttcttct tctagggggac ctg                                              23
```

METHOD OF AMPLIFYING NUCLEIC ACID FROM BLOOD

This application claims priority to Korean Patent Application No. 10-2006-0050478, filed on Jun. 5, 2006, and all the benefits accruing therefrom under 35 U.S.C. §119, the contents of which are incorporated herein in its entirety by reference.

BACKGROUND OF THE INVENTION

1. Field of the Invention

The present invention relates to a method of amplifying nucleic acid from blood.

2. Description of the Related Art

In order to efficiently amplify or detect target nucleic acid, nucleic acid first needs to be separated from a sample, as materials that obstruct a Polymerase Chain Reaction ("PCR") exist in the sample. An example of the material that obstructs the PCR is a red blood cell. Therefore, the amount of blood directly used in the PCR is limited. If blood makes up 1.5% of a total reaction solution, PCR products cannot be obtained effectively.

In order to overcome this problem, a method of selectively destroying red blood cells may be used. U.S. Pat. No. 4,407,942 discloses a method of selectively destroying red blood cells using ammonium chloride.

U.S. Pat. No. 5,704,884 discloses a method including a) mixing a whole blood sample with a red blood cell destroying solution. The destroying solution has a pH of 6 to 8 and includes ammonium chloride of 50 to 100 millimoles (mM) and a monocarboxylic acid of 0.01 to 0.1 parts by weight or a salt thereof; b) centrifuging the obtained mixture to form leukocyte pellets from the whole blood sample; c) removing supernatant from the whole blood sample in order to wash the leukocyte pellets in a fresh destroying solution sample; and d) centrifuging the leukocyte pellets to separate them from the fresh destroying solution sample. All the operations a) through d) are performed within 20 minutes.

U.S. Pat. No. 5,935,825 discloses a PCR amplifying method in which a PCR is performed at a relatively higher pH than the pH used in many methods.

U.S. Pat. No. 6,284,117 discloses an apparatus and a method of reducing an ionic strength of a low volume solution used in the electronic transport of nucleic acid, protein and/or cells. The apparatus includes a tube shaped molecular weight cut-off membrane having lumen, an ion-exchange resin, an electrodialysis electrode, and a chamber surrounding and housing the cut-off membrane, the ion-exchange resin, the electrodialysis electrode. The cut-off membrane has inlet and outlet ports leading through the chamber and is embedded in the ion-exchange resin and the center of the ion-exchange resin. The chamber has inlet and outlet ports to allow materials to flow and be exchanged inside and outside the chamber, and the electrodialysis electrode is disposed in the opposite side of the chamber with respect to the membrane in a spaced axial alignment. The method includes applying current between the electrodialysis electrodes.

However, a method of using a large amount of blood directly in a PCR is not disclosed in the conventional art.

BRIEF SUMMARY OF THE INVENTION

An exemplary embodiment provides a method of efficiently amplifying target nucleic acid from blood using electrolysis.

An exemplary embodiment provides a method of efficiently amplifying target nucleic acid from blood using electrolysis.

In an exemplary embodiment, there is provided a method of amplifying nucleic acid from blood. The method includes performing electrodialysis on a blood sample and reducing an ionic strength of the sample, and performing a Polymerase Chain Reaction ("PCR") using the blood sample on which the electrodialysis is performed as a template.

In an exemplary embodiment, the performing the electrodialysis may include injecting blood into a diluting compartment including molecular weight cut-off membranes disposed in a wall of the diluting compartment, and applying a voltage between membranes and moving ionic materials into a concentrating compartment from the diluting compartment.

In an exemplary embodiment, the molecular weight cut-off membrane may have a molecular weight cut-off of about 1 kilo-Dalton (kDa) to about 500 kilo-Daltons (kDa).

In an exemplary embodiment, the voltage may be direct voltage ("DC").

In an exemplary embodiment, the diluting compartment may include two walls facing each other formed of the molecular weight cut-off membranes.

In an exemplary embodiment, the voltage may be about 10 volts (V) to about 200 volts (V).

In an exemplary embodiment, the electrodialysis may be performed for about seconds to about minutes, for example less than 200 seconds/1 ml blood sample. However, the period for performing the electrodialysis depends on the intensity of voltage and current and the volume of the solution, and a person skilled in the art would determine suitable period for the performance based the above parameters.

In an exemplary embodiment, the PCR may be performed using blood making up about 0.1% to about 30% (v/v) of a reaction solution as the template. The electrodialysis is performed on the blood samples.

In an exemplary embodiment of the method of amplifying nucleic acid from blood may further include performing electrolysis on a blood sample before performing the electrodialysis or performing the electrolysis on the electrodialyzed blood sample after performing the electrodialysis.

In an exemplary embodiment, the electrolysis may include adding the sample including blood or blood on which the electrodialysis is performed into a cathode chamber and applying a voltage therein.

In an exemplary embodiment, the voltage of the electrolysis may be about 1 (V) to about 100 V.

In an exemplary embodiment, the electrolysis may be performed for about seconds to about minutes, for example less than 200 seconds/1 ml blood sample. However, the period for performing the electrolysis depends on the intensity of voltage and current and the volume of the solution, and a person skilled in the art would determine suitable period for the performance based the above parameters.

An exemplary embodiment provides a method of amplifying nucleic acid from blood. The method includes performing electrolysis on a blood sample and performing a PCR using the blood sample on which the electrolysis is performed as a template.

In an exemplary embodiment, the electrolysis may include adding the sample including blood into a cathode chamber and applying a voltage therein.

In an exemplary embodiment, the voltage of the electrolysis may be about 1 volt (V) to about 100 volts (V).

In an exemplary embodiment, the electrolysis may be performed for about seconds to about minutes, for example less than 200 seconds/1 ml blood sample. However, the period for performing the electrolysis depends on the intensity of voltage and current and the volume of the solution, and a person skilled in the art would determine suitable period for the performance based the above parameters.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
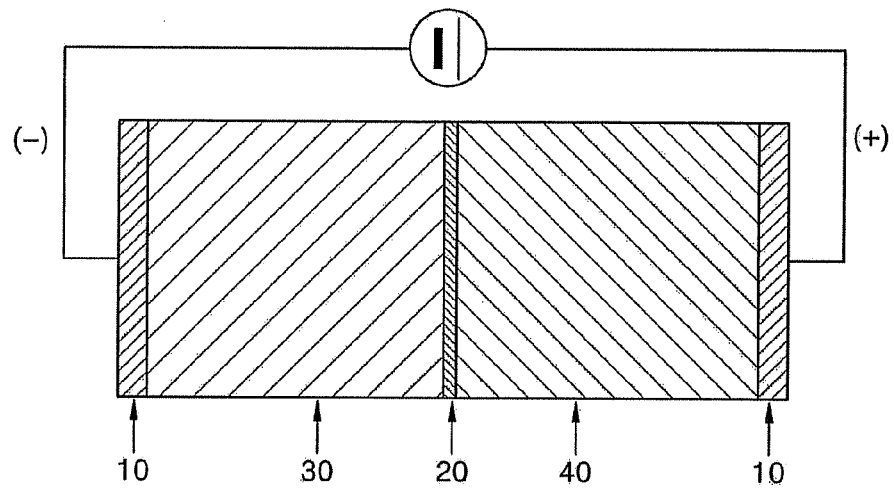
FIG. 1 is a diagram of an exemplary embodiment of an electrolysis device according to the present invention.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the present invention will be described more fully with reference to the accompanying drawings, in which exemplary embodiments of the invention are shown.

An exemplary embodiment of a method of amplifying nucleic acid from blood, includes performing an electrodialysis on a blood sample to reduce an ionic strength of the sample, and performing a Polymerase Chain Reaction ("PCR") using the blood sample after the electrdodialysis. The blood sample upon which electrodialysis is performed may be used as a template (e.g., primer hybridized with a strand of target nucleic acid) in the PCR.

The method includes performing electrodialysis on a blood sample and reducing an ionic strength of the blood sample. When the electrodialysis is performed on the blood sample, ionic materials included in blood are removed. The removing the ionic materials reduces the ionic strength of the blood sample. Advantageously, ionic materials that obstruct the PCR are removed from the sample. The ionic materials may be stored and liquefied, thereby destroying red blood cells in the sample.

In an exemplary embodiment, an electrodialytic apparatus may include ion exchange membranes. These membranes facilitate specific ions to pass through the membranes under a polarized electric field. When the membranes are used, a fluid having high concentration and undesired ions passes through a compartment in which ion exchange membranes are included in one or more of the compartment walls. "Electrodialysis" is well known in the field to which the present invention pertains and refers to a method, wherein a sample containing salt is placed between membranes and an electric field is applied thereto. The cations and anions of the sample migrate in opposite directions and pass through the membranes, leaving purer water between the membrane filters. The electrodialysis apparatus conventionally comprises three chambers defined by membranes. Two side chambers with electrodes have pure water. The cations and anions of the sample are transported through membrane from middle chamber to side chambers using electric field.

As the fluid passes through the compartment, ions are removed to an adjacent compartment. A compartment where ions are removed is called a diluting compartment and a compartment where ions are moved into is called a concentrating compartment. When ion separation having low efficiency is sufficient for a process such as cell disruption, ion exchange membranes can be replaced with tube shaped molecular weight cut-off membranes. In an exemplary embodiment, the molecular weight cut-off membrane includes an ion exchange membrane.

The operation of performing electrodialysis may include injecting blood into the diluting compartment in which the molecular weight cut-off membranes are included in one or more of the compartment walls, and applying a voltage between membranes such that ionic materials move into the concentrating compartment from the diluting compartment.

Any of a number of materials may be used in the molecular weight cut-off membrane as is suitable for the purpose described herein, such as for freely transporting ionic materials with low molecular weight, protein, nucleic acid, and/or cells. The cut-off of the molecular weight cut-off membrane varies according to the materials to be removed. In an exemplary embodiment, the cut-off of the molecular weight cut-off membrane is not particularly restricted and may have cut-off range of about 1 kilo-Dalton (kDa) to about 500 kilo-Daltons (kDa). The molecular weight cut-off membrane may include or be formed of reproduced cellulose, polyethersulfone ("PES"), polysulfone ("PS"), or polyvinyl difluoride ("PVDF") but the invention is not limited thereto.

In an exemplary embodiment, a voltage used in the electrodialysis is direct voltage. The direct voltage may be applied with a voltage of about 10 volts (V) to about 200 volts (V) for several seconds to several minutes, for example less than 200 seconds/1 ml blood sample. However, the period for performing the electrodialysis depends on the intensity of voltage and current and the volume of the solution, and a person skilled in the art would determine suitable period for the performance based the above parameters.

The method of the present invention includes performing the PCR using the blood sample on which electrodialysis is performed as a template.

In the PCR, primer is hybridized with a strand of target nucleic acid (also referred to as "template") under the presence of a polymerization agent such as deoxyribonucleic acid ("DNA") polymerase and deoxyribonucleotide phosphate (dNTP). Once primer extension products are denatured, a copy of the template is produced and a cycle of annealing, extending, and denaturalizing is performed for desired times in order to exponentially increase the amount of nucleic acid having the same sequence as the target nucleic acid.

The blood samples on which the electrodialysis is performed, may be used as the template of the PCR reaction without an additional operation of extracting protein. In exemplary embodiments, the PCR may be performed using about 0.1% to about 30% (v/v) of the blood samples of a reaction solution as the template. In one exemplary embodiment the PCR is performed using about 0.5% to about 20% (v/v) of the blood samples.

An exemplary embodiment of the method may further include performing the electrolysis on a blood sample before performing the electrodialysis. Alternatively, the method may further include performing electrolysis on the blood sample on which the electrodialysis is performed after the electrodialysis is performed.

In electrolysis, electrolyte solutions are added to each of a cathode chamber and an anode chamber separated by an ion-permeable membrane and a voltage is applied thereto. A reaction occurs in an involuntary direction by current applied due to the voltage. "Electrolysis" is well known in the field to which the present invention pertains and refers to a method, comprising passing an electric current through a solution containing salts and generating ions by an oxidation and reduction reaction. In reaction, reduction reaction occurs at the cathode electrode and oxidation reaction occurs at the anode electrode.

In an exemplary embodiment, performing the electrolysis may include adding the sample including blood or blood on which the electrodialysis is performed into the cathode chamber and applying the voltage therein. The voltage and time may be about 1 V to about 100 V and about several seconds to about several minutes, respectively, for example less than 200 seconds/1 ml blood sample but are not limited thereto. However, the period for performing the electrolysis depends on the intensity of voltage and current and the volume of the solution, and a person skilled in the art would determine suitable period for the performance based the above parameters. Due to the electrolysis, protein included in the blood chamber in the cathode chamber or the chamber in which the electrodialysis is performed, is denatured and lipid components of the membrane are dissolved. However, the present invention is not particularly restricted thereto.

In an exemplary embodiment of a method of amplifying nucleic acid from blood, includes performing electrolysis on a blood sample and performing the PCR using the blood sample on which the electrolysis is performed as a template.

In the method of amplifying nucleic acid from, the electrolysis may be performed by adding the sample including blood or blood on which the electrodialysis is performed into a cathode chamber and applying voltage therein. The voltage and time applied may be about 1 V to about 100 V and about several seconds to about several minutes for example less than 200 seconds/1 ml blood sample, respectively, but are not limited thereto. However, the period for performing the electrolysis depends on the intensity of voltage and current and the volume of the solution, and a person skilled in the art would determine suitable period for the performance based the above parameters.

The present invention will be described in greater detail with reference to the following examples. The following examples are for illustrative purposes only and are not intended to limit the scope of the invention.

EXAMPLE 1

Electrolysis of Blood

In this example, the cathode chamber was filled with whole blood in order to perform the electrolysis thereon and then was observed in terms of how the electrolysis affected the blood.

FIG. 1 is a diagram of an exemplary embodiment of an electrolysis device used according to the present invention. Referring to FIG. 1, the device includes a cathode chamber 30, an anode chamber 40, and a cellophane film 20. The cellophane film 20 is a molecular weight cut-off membrane and is interposed between the cathode chamber 30 and the anode chamber 40. The cathode chamber 30 and the anode chamber 40 are connected with a power source through electrodes 10, respectively. 5 milliliters (ml) of 300 mM $Na_2SO_4$ was filled in the anode chamber 40 as an electrolyte, and 5 ml of human blood was filled in the cathode chamber 30.

Figure 2:
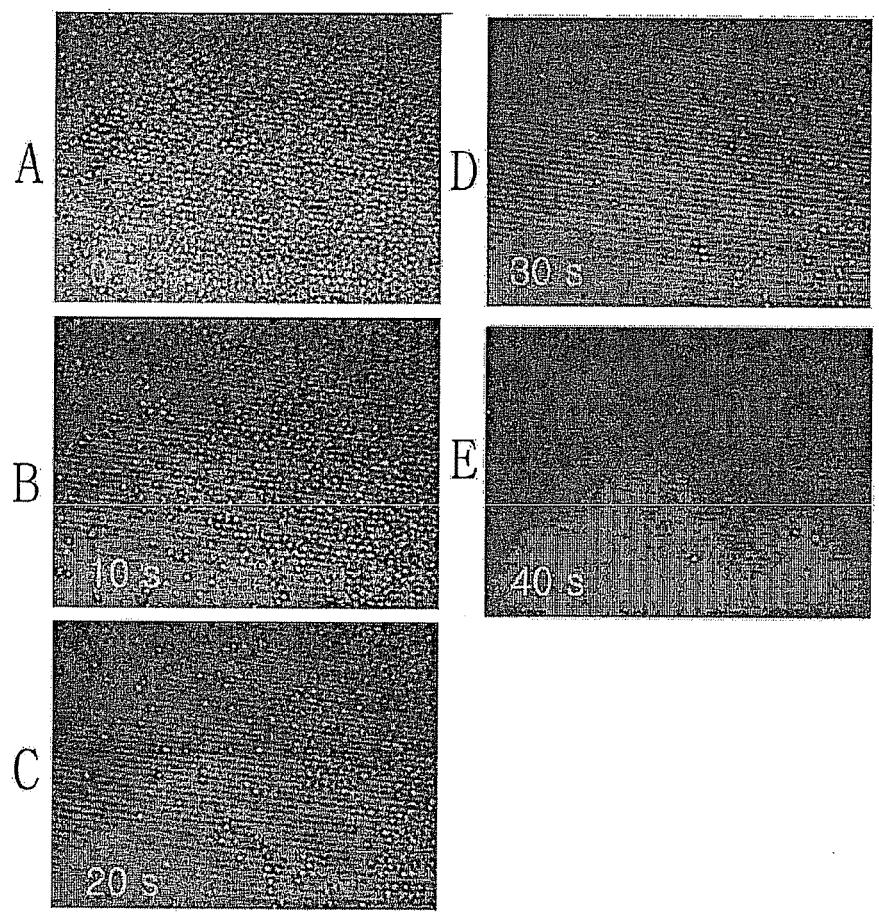
FIG. 2 are photographs showing results after observing samples in which a voltage of 20 V is applied through a power source and a current of 10 mA is applied for 40 seconds.

FIG. 2 includes photographs showing results after observing the samples in which a voltage of 20 V is applied through the power source and a current of 10 milliamperes (mA) is applied for 40 seconds. Referring to FIG. 2, as the electrolysis was performed on the samples, blood cells were disrupted and blood color became transparent. The color change occurs due to denaturation of heme by the electrolysis. The heme is originated from the red blood cells.

EXAMPLE 2

Electrodialysis of Blood

In this example, whole blood was filled in a diluting compartment to perform the electrodialysis thereon and then was observed in terms of how the electrodialysis affected the blood.

Figure 3:
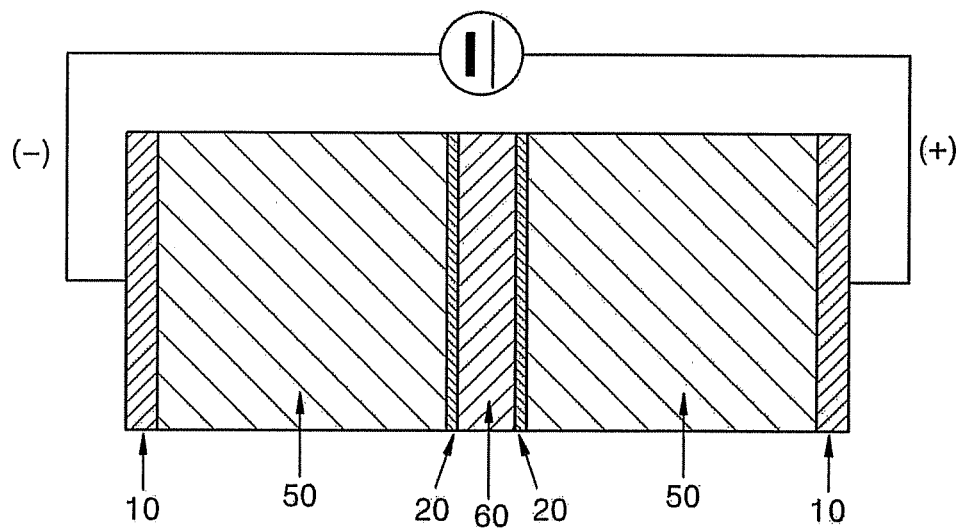
FIG. 3 is a diagram of an exemplary embodiment of an electrodialytic apparatus according to the present invention.

FIG. 3 is a diagram of an exemplary embodiment of an electrodialytic apparatus according to the present invention. Referring to FIG. 3, the apparatus includes a diluting compartment 60 in which both walls thereof are formed of a cellophane film 20, e.g., a molecular weight cut-off membrane, and two concentrating compartments 50 adjacent to the diluting compartment 60 and facing each other relative to the diluting compartment 60. The concentrating compartments 50 are connected (e.g., electrically) with the electrodes 10. A distance between the electrodes 10 is 6 centimeters (cm) and the area of the electrodes 10 was 80 cm². 200 ml of distilled water was filled in the concentrating compartment 50 and 5 ml of human blood was filled in the diluting compartment 60.

A voltage of 100 V was applied to both the concentrating and diluting compartments 50 and 60 for 15 minutes. When conductivity at the concentrating compartments 50 was significantly raised indicating a relatively excessive amount of current flowed, distilled water was circulated in the two concentrating compartments 50 in order to reduce the conductivity. The maximum current was 100 mA or below.

Figure 4:
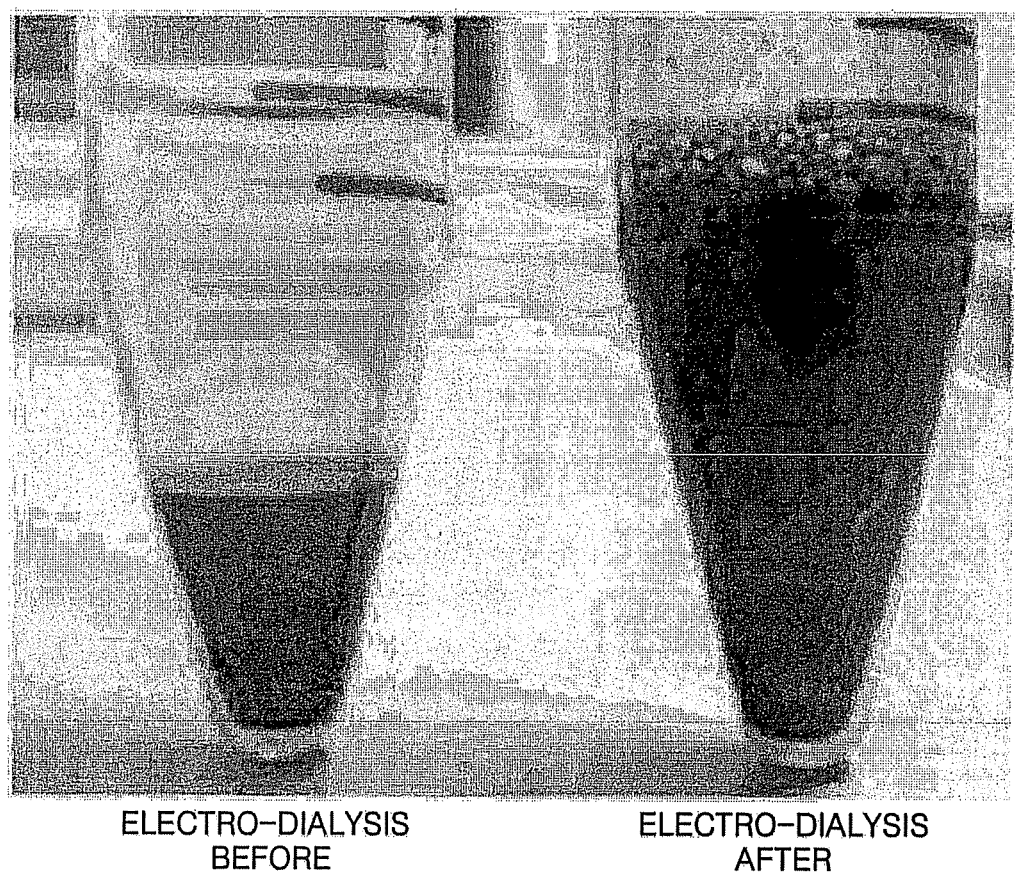
FIG. 4 is a photograph showing a result after an electrodialysis is performed on blood by applying a voltage of 100 V and then, spinning-down.

FIG. 4 is a photograph showing a result after electrodialysis is performed on blood by applying a voltage of 100 V for 15 minutes and then, spinning-down the sample. Referring to FIG. 4, red blood cells were disrupted by the electrodialysis. Ionic materials were moved from the diluting compartment 60 to the concentrating compartment 50 so as to reduce the ionic strength of blood and thus, red blood cells were disrupted. Advantageously, red blood cells can be disrupted using the electrodialysis without diluting blood.

EXAMPLE 3

PCR Using Blood Including *Escherichia Coli* DNA as Template

In this example, blood was treated using various methods and the PCR was performed using blood samples including *Escherichia coli* DNA with a concentration of 1000 *Escherichia coli*/μl as a template.

The blood used as a template was untreated blood, blood on which the electrolysis was performed, blood on which the electrodialysis was performed, and blood on which the electrolysis was performed after the electrodialysis. The device of Example 1 was used in the electrolysis. 2 ml of blood was filled into the cathode chamber 30 and 2 ml of Na₂SO₄ was filled into the anode chamber 40. Then a voltage of 50 V was applied to the chambers for 15 minutes in order to have a maximum current of 30 mA.

The apparatus of Example 2 was used in the electrodialysis. 5 ml of blood was filled in the diluting compartment 60 and 200 ml of distilled water was added to the two adjacent concentrating compartments 50. Then, a voltage of 100 V was applied to the compartments. The electrolysis performed after the electrodialysis was performed was the same as described above.

The PCR was performed using various amounts of blood, which was treated using various methods, as a template without extracting protein. Primer used in the PCR was oligonucleotide having nucleotide sequence of SEQ ID NO: 1 and SEQ ID NO: 2 (the target sequence was *Escherichia coli* genome DNA) and the conditions of the PCR are as follows.

The PCR was performed at an initial denaturation under 95° C. for 1 minute, a denaturation under 95° C. for 5 seconds, an annealing under 62° C. for 13 seconds, and extension under 72° C. for 15 seconds and the whole process was repeated 30 times. Then, final extension was performed under 72° C. for 1 minute. The composition of the PCR reactants is illustrated in Table 1.

TABLE 1

| Components (μl) | Sample 1 | Sample 2 | Sample 3 | Sample 4 | Sample 5 | Sample 6 |
|---|---|---|---|---|---|---|
| 1x buffer | 5 | 5 | 5 | 5 | 5 | 5 |
| dNTP | 1 | 1 | 1 | 1 | 1 | 1 |
| Forward primer | 1 | 1 | 1 | 1 | 1 | 1 |
| Reverse primer | 1 | 1 | 1 | 1 | 1 | 1 |
| BSA | 5 | 5 | 5 | 5 | 5 | 5 |
| Taq polymerase | 0.5 | 0.5 | 0.5 | 0.5 | 0.5 | 0.5 |
| Distilled water | 35.25 | 35 | 34 | 33 | 30.5 | 20.5 |
| *E.coli* DNA | 1 | 1 | 1 | 1 | 1 | 1 |
| Sample | 0.25 | 0.5 | 1.5 | 2.5 | 5 | 15 |
| Total volume | 50 | 50 | 50 | 50 | 50 | 50 |
| Blood volume percent (%) | 0.5 | 1 | 3 | 5 | 10 | 30 |

Figure 5:
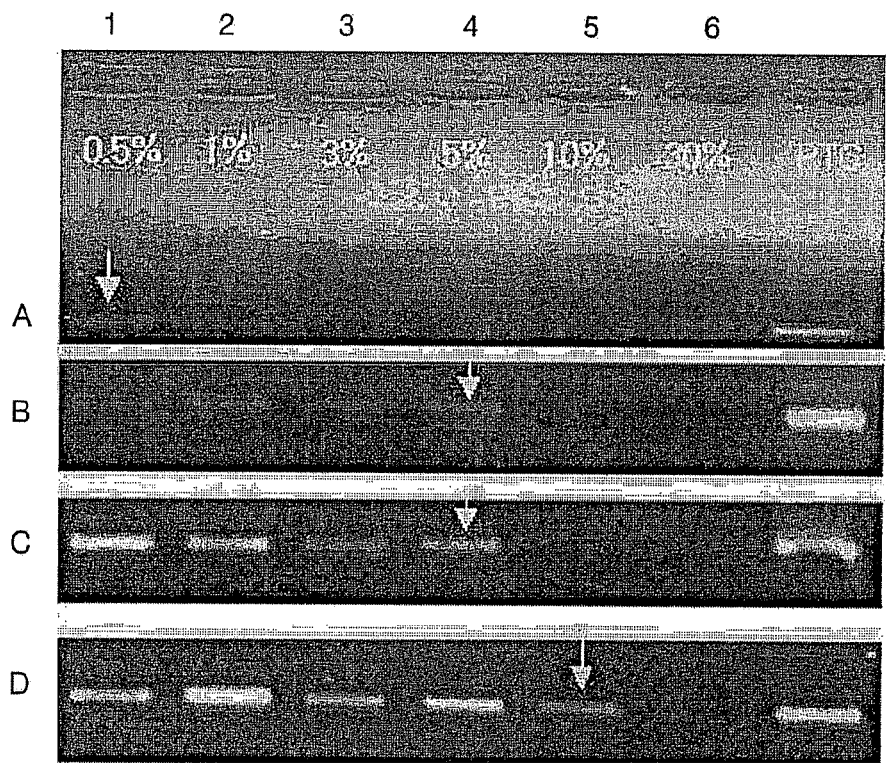
FIG. 5 is a photograph showing a result of a Polymerase Chain Reaction ("PCR") in which respective blood samples are used in a range of 0.5% to 30% (v/v) of the total volume of the PCR reactants.

FIG. 5 is a photograph showing a result of the PCR in which respective blood samples are used in a range of 0.5 to 30% (v/v) of the total volume of the PCR reactants. Referring to FIG. 5, when blood was added by an amount of 0.5% (v/v) of the total volume of the PCR reactants, PCR products were obtained and when the blood was added by an amount above 0.5% (v/v) of the total volume of the PCR reactants, PCR products were not obtained (A).

When the blood samples were treated by the electrolysis or electrodialysis, respectively and were added by an amount of up to 5% (v/v) of the PCR reactants, PCR products were obtained (B or C). When the blood sample was treated by the electrolysis after the electrodialysis and was added by an amount of up to 10% (v/v) of the PCR reactants, PCR products were obtained (D).

When untreated blood was used by an amount of up to 30% (v/v) of the PCR reactants, blood was solidified during the PCR, however, if blood was treated by one of electrolysis and electrodialysis, blood was not solidified (not illustrated).

EXAMPLE 4

PCR Using Blood Including *Escherichia Coli* as Template

In this example, blood including *Escherichia coli* was treated using various methods and the PCR was performed using the blood as a template.

The blood used as a template was untreated blood, blood on which the electrolysis was performed, blood on which the electrodialysis was performed, and blood on which the electrolysis was performed after electrodialysis, the blood including *Escherichia coli* with the concentration of 1,000 *Escherichia coli*/μl, 100 *Escherichia coli*/μl, and 10 *Escherichia coli*/μl, respectively.

The device of Example 1 was used in the electrolysis. 2 ml of blood was filled in the cathode chamber 30 and 2 ml of Na₂SO₄ was filled in the anode chamber 40. A voltage of 50 V was applied to the chambers for 15 minutes so as to have a maximum current of 30 mA.

The apparatus of Example 2 was used in the electrodialysis. 5 ml of blood was filled into the diluting compartment 60 and 200 ml of distilled water was added to the two adjacent concentrating compartments 50. Then, the voltage of 100 V was applied to the compartments. The electrolysis performed after the electrodialysis was performed was the same as described above.

The PCR was performed using various amounts of blood, which was treated using various methods, as a template without extracting protein. Primer used in the PCR was oligonucleotide having nucleotide sequence of SEQ ID NO: 1 and SEQ ID NO: 2 (the target sequence was *Escherichia coli* genome DNA) and the conditions of the PCR are as follows.

The PCR was performed at an initial denaturation under 95° C. for 1 minute, a denaturation under 95° C. for 5 seconds, an annealing under 62° C. for 13 seconds, and extension under 72° C. for 15 seconds and repeated 30 times. Then, the final extension was performed at under 72° C. for 1 minute. The composition of the PCR reactants is illustrated in Table 2.

TABLE 2

| Components (μl) | Sample 1 | Sample 2 | Sample 3 | Sample 4 |
|---|---|---|---|---|
| 1×buffer | 5 | 5 | 5 | 5 |
| dNTP | 1 | 1 | 1 | 1 |
| Forward primer | 1 | 1 | 1 | 1 |
| Reverse primer | 1 | 1 | 1 | 1 |
| BSA | 5 | 5 | 5 | 5 |
| Taq polymerase | 0.5 | 0.5 | 0.5 | 0.5 |
| Distilled water | 35 | 34 | 31.5 | 26.5 |
| Sample | 1.5 | 2.5 | 5 | 10 |
| Total volume | 50 | 50 | 50 | 50 |
| Blood volume percent (%) | 3 | 5 | 10 | 20 |

Figure 6:
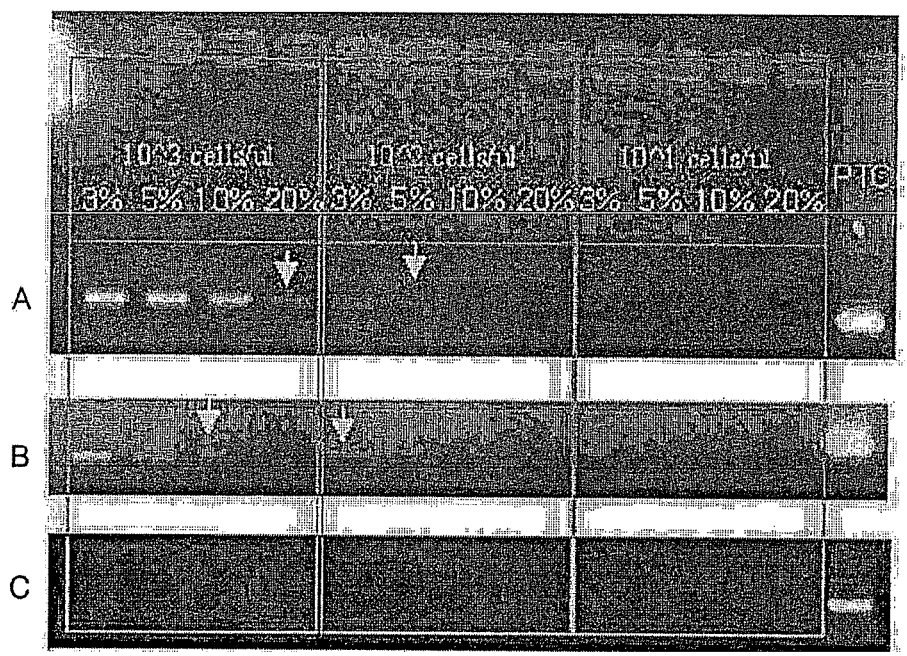
FIG. 6 is a photograph showing a result of a PCR in which respective blood samples are used by an amount of 3% to 20% (v/v) of the total volume of the PCR reactants.

FIG. 6 is a photograph showing a result of the PCR in which respective blood samples are used by an amount of 3% to 20% (v/v) of the total volume of the PCR reactants. Referring to FIG. 6, when untreated blood was added by an amount of 3% (v/v) of the total volume of the PCR reactants irrespective of the concentration of *Escherichia coli*, PCR products were not obtained (C). The PCR does not occur due to materials included in blood that obstruct PCR.

When the blood samples with the concentration of 100 *Escherichia coli*/μl and 1,000 *Escherichia coli*/μl were treated by the electrolysis only and were added by an amount of up to 3% (v/v) and 10% (v/v) of the PCR reactants, respectively, PCR products can be obtained (B). Moreover, when the blood samples with the concentration of 100 *Escherichia coli*/μl and 1,000 *Escherichia coli*/μl were treated by the electrolysis after the electrodialysis and were added by an amount of up to 5% and 20% of the PCR reactants, respectively, PCR products can be obtained (A). These results indicate that the PCR is possible in blood having higher concentration than the blood used herein.

Figure 7:
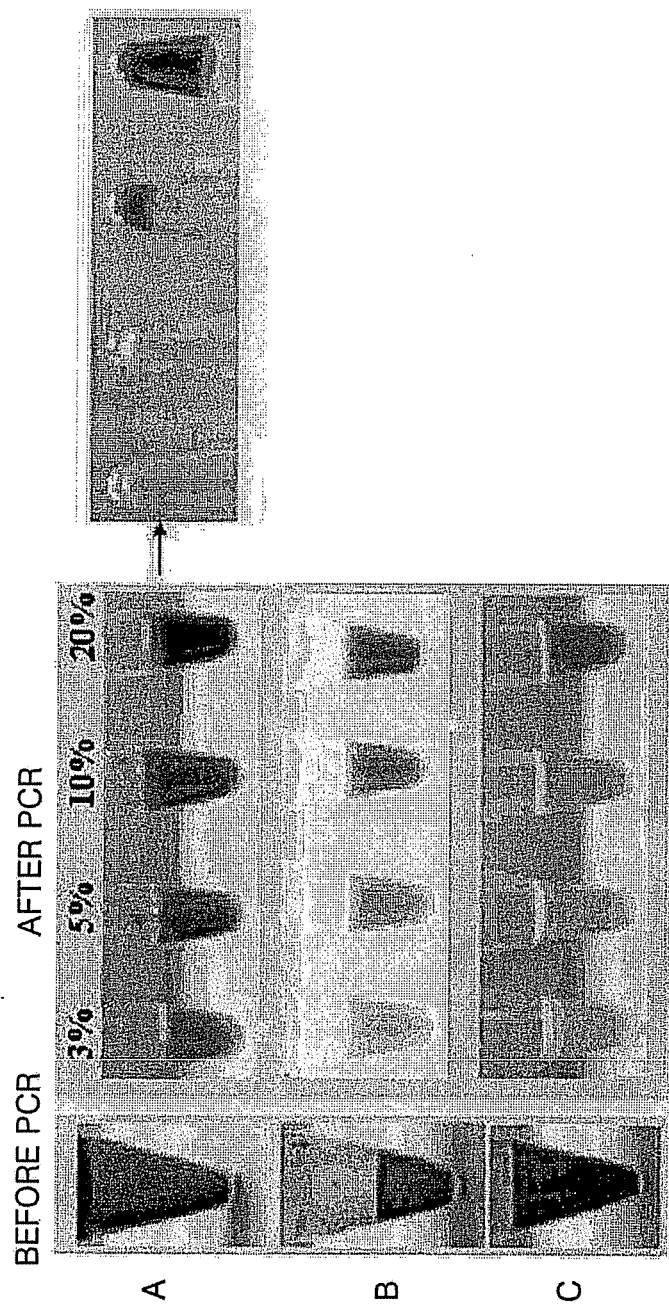
FIG. 7 are photographs showing PCR reaction solutions obtained after respective blood samples including *Escherichia coli* with a concentration of 1000 *Escherichia coli*/μl are treated differently by adding an amount of 3% to 20% (v/v) of the PCR reaction solutions into the PCR reaction solutions.

FIG. 7 are photographs showing PCR reaction solutions obtained after respective blood samples including *Escherichia coli* with a concentration of 1000 *Escherichia coli*/μl are treated differently by adding an amount of 3 to 20% (v/v) of the PCR reaction solutions into the PCR reaction solutions. Referring to FIG. 7, when untreated blood was added by an amount of 3% (v/v) or above and up to 20% (v/v) into the PCR reaction solutions, respectively, the color darkened and blood was solidified, respectively. The color got lighter in the blood treated by the electrolysis, and the color got lighter than the blood treated by the electrolysis in the blood treated by the electrolysis after the electrodialysis.

As in the illustrated embodiment, when blood is treated by at least one of electrolysis and electrodialysis, a PCR significantly progresses. In a method of amplifying nucleic acid from blood, a relatively large amount of blood can be used in the PCR reaction solution as a template and amplifying efficiency can be increased. Advantageously, target nucleic acid included in blood, such as bacteria or virus, can be efficiently detected.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of amplifying nucleic acid from blood, the method comprising:
   performing electrodialysis on a blood sample thereby reducing an ionic strength of the sample and disrupting red blood cells present in the blood sample;
   performing electrolysis on the blood sample before or after performing the electrodialysis, and
   performing a Polymerase Chain Reaction ("PCR") using the blood sample on which the electrodialysis and the electrolysis has been performed as a template, wherein the blood sample used as the template in the PCR makes up 5% to 20% by volume of a PCR reaction solution,
   wherein the performing electrodialysis comprises injecting the blood sample into a diluting compartment including molecular weight cut-off membranes disposed in a wall of the diluting compartment, and applying a voltage between the membranes and moving ionic materials into a concentrating compartment from the diluting compartment and wherein the voltage is direct voltage ("DC").

2. The method of claim 1, wherein the molecular weight cut-off membranes have a molecular weight cut-off of about 1 kilo-Dalton (kDa) to about 500 kilo-Daltons (kDa).

3. The method of claim 1, wherein the diluting compartment includes two walls facing each other, the molecular weight cut-off membranes being disposed in both of the two walls.

4. The method of claim 1, wherein the voltage is about 10 volts (V) to about 200 volts (V).

5. The method of claim 1, wherein the electrodialysis is performed for about less than 200 seconds/ml blood sample.

6. The method of claim 1, when the electrolysis is performed before performing electrodialysis, the performing electrolysis comprises:
   adding the blood sample including blood into a cathode chamber; and
   applying a voltage therein.

7. The method of claim 6, wherein the voltage is about 1 V to about 100 V.

8. The method of claim 7, wherein the electrolysis is performed for about less than 200 seconds/ml blood sample.

9. The method of claim 1, when the electrolysis is performed after performing the electrodialysis, the performing electrolysis comprises:
   adding the sample including blood on which the electrodialysis is performed into a cathode chamber; and
   applying a voltage therein.

10. The method of claim 9, wherein the voltage is about 1 V to about 100 V.

11. The method of claim 10, wherein the electrolysis is performed for about less than 200 seconds/ml blood sample.

* * * * *